United States Patent [19]
Robinson et al.

[11] Patent Number: 5,603,923
[45] Date of Patent: *Feb. 18, 1997

[54] ARTIFICIAL TANNING COMPOSITIONS HAVING IMPROVED COLOR DEVELOPMENT

[75] Inventors: Larry R. Robinson, Lebanon; Paul R. Tanner, Maineville, both of Ohio

[73] Assignee: The Procter & Gamble Company, Cincinnati, Ohio

[*] Notice: The term of this patent shall not extend beyond the expiration date of Pat. No. 5,514,437.

[21] Appl. No.: 533,023

[22] Filed: Sep. 25, 1995

Related U.S. Application Data

[63] Continuation of Ser. No. 219,061, Mar. 29, 1994.

[51] Int. Cl.$^6$ .................. A61K 7/44; A61K 7/42
[52] U.S. Cl. .................. 424/60; 424/59; 424/63
[58] Field of Search .................. 424/59, 60, 63

[56] References Cited

U.S. PATENT DOCUMENTS

| | | | |
|---|---|---|---|
| 2,274,725 | 3/1942 | Meeker et al. | 424/59 |
| 2,949,403 | 8/1960 | Andreadis . | |
| 3,177,120 | 4/1965 | Black . | |
| 3,184,388 | 5/1965 | Kalopissis . | |
| 3,272,713 | 9/1966 | Runge . | |
| 3,920,808 | 11/1975 | Fusaro | 424/59 |
| 4,145,413 | 3/1979 | Usdin et al. | 424/63 |
| 4,293,543 | 10/1981 | Cotte et al. | 424/59 |
| 4,419,343 | 12/1983 | Pauly | 424/59 |
| 4,434,154 | 2/1984 | McShane | 424/60 |
| 4,832,943 | 5/1989 | Grollier et al. | 424/59 |
| 4,847,267 | 7/1989 | Deckner et al. | 514/311 |
| 5,100,660 | 3/1992 | Hawe et al. | 424/78.35 |
| 5,221,530 | 6/1993 | Janchitraponveg et al. | 424/70 |
| 5,232,688 | 8/1993 | Ziegler et al. | 424/59 |
| 5,302,378 | 4/1994 | Crotty et al. | 424/59 |

FOREIGN PATENT DOCUMENTS

| | | | |
|---|---|---|---|
| 90/61950 | 5/1991 | Australia | A61K 7/02 |
| 103635 | 3/1969 | Czechoslovakia | A61K 62/00 |
| 227012 | 7/1987 | European Pat. Off. | A61K 7/00 |
| 456545 | 4/1991 | European Pat. Off. | A61K 7/42 |
| 547864 | 6/1993 | European Pat. Off. | A61K 7/42 |
| 622070A1 | 11/1994 | European Pat. Off. | A61K 7/42 |
| 1252400 | 12/1960 | France . | |
| 06227937 | 8/1994 | Japan | 424/59 |
| 132150 | 10/1982 | Spain | A61K 62/04 |
| 825600 | 1/1983 | U.S.S.R. | A61K 7/00 |
| WO92/17159 | 10/1992 | WIPO | A61K 7/42 |
| WO93/09215 | 5/1993 | WIPO | C11D 3/04 |
| 94/22419 | 10/1994 | WIPO | A61K 7/42 |

OTHER PUBLICATIONS

Technical Bulletin—Salcare SC 92 for Cosmetic/Personal Care applications, Allied Colloids, Suffolk, VA—Undated.
M. S. Balsam et al., (ed.) *Cosmetic Science and Technology* 2nd edition, Dec. 10, 1973, vol. 1, pp. 293–305 Wiley–Interscience, New York.
Merck German Technical Data sheet, Nov. 24, 1993.
Kawashima et al., "Nonenzymatic Browning Reactions of Dihydroxyacetone with Amino Acide of Their Esters", *Agric. Biol, Chem.*, 44(7), 1595–1599 (1980).
Ingredient label from packaging, Bain de Soleil Tanning Creme, copyright 1993.
A. Meybeck, "A Spectroscopic Study of the Reaction Products of Dihydroxyacetone with Amine Acids", *J. Soc. Cosmet. Chem.*, 28, 25–35 (1977).
E. Wittgenstein et al., "Reaction of Dihydroxyacetone (DHA) with Human Skin Callus and Amino Compounds", *J. Invest. Derm.*, 23, 283–286 (1961).
M. F. Bobin et al., "Effects of Color Adjuvants on the Tanning Effect of Dihydroxyacetone", *J. Soc. Cosmet. Chem.*, 35, 265, 272 (Aug. 1984).
Ingredient label from Elizabeth Arden's Spa for the Sun Self Tanner SPF 15 Product, no copyright dated available.
*The Merck Index*, Tenth Edition, 1983, Entry 8476.
V. R. Usdin, "Artificial Tanning Preparations", *Cosmetics and Toiletries*, vol. 91, Mar. 1976 pp. 29–32.
J. Buchter et al., "The Reaction of Dihydroxyacetone with Proteins", *American Perfumer*, Dec., 1960, pp. 46–48.
N. Kanas et al., "Factors Influencing the Tanning Effect of Dihydroxyacetone on the Skin", *American Perfumer*, Nov. 1960, pp. 33–34.
M. Fleming et al., "Chemistry of Browning Reaction", *The Sugar Journal*, Apr. 1971, pp. 21–27.
K. Laden et al., "The Reaction of α–Hydroxymethyl Ketones with Skin and Amino Acids", *J. Soc. Cosmetic Chemists*, 16, 777–782 (1965).

*Primary Examiner*—Shelley A. Dodson
*Attorney, Agent, or Firm*—Anthony D. Sabatelli; David K. Dabbiere

[57] ABSTRACT

The present invention relates to artificial tanning compositions that provide improved color development and good chemical and physical stability. These compositions comprise dihydroxyacetone, certain amino acids or their pharmaceutically acceptable salts, and a topical carrier, wherein said compositions have a pH value of less than about 4. In other embodiments these compositions comprise dihydroxyacetone, certain amino acids or their pharmaceutically acceptable salts, and a stabilizing salt selected from the group consisting of metabisulfite salts, sulfite salts, hydrogen sulfite salts, and mixtures thereof, and a topical carrier.

29 Claims, No Drawings

ARTIFICIAL TANNING COMPOSITIONS HAVING IMPROVED COLOR DEVELOPMENT

This is a continuation of application Ser. No. 08/219,061, filed on Mar. 29, 1994.

The present invention relates to compositions useful for providing an artificial tan to human skin. These compositions have improved color development characteristics compared to conventional artificial tanning compositions utilizing dihydroxyacetone as the sole artificial tanning active and improved stability compared to compositions utilizing dihydroxyacetone in combination with other color-modifying adjuvants.

In one set of embodiments, the compositions of the present invention comprise dihydroxyacetone, certain amino acids or their pharmaceutically acceptable salts, and a topical carrier, wherein the compositions have a pH value less than about 4. These compositions can also comprise a sunscreen agent and are useful for protecting the skin from the harmful effects of ultraviolet radiation.

In other embodiments these compositions comprise dihydroxyacetone, certain amino acids or their pharmaceutically acceptable salts, a stabilizing salt selected from the group consisting of metabisulfite salts, sulfite salts, and hydrogen sulfite salts, and a topical carrier. In these other embodiments, the compositions are not restricted to having a pH value less than about 4. These compositions can also comprise a sunscreen agent and are useful for protecting the skin from the harmful effects of ultraviolet radiation.

BACKGROUND OF THE INVENTION

A sun-tanned appearance is a symbol of a healthy, dynamic, and active life. Yet, the damaging effects of sunlight and other sources of ultraviolet radiation on the skin are well documented. These effects are cumulative and potentially serious, and include sunburn, skin cancer, and premature aging of the skin. These effects associated with exposure to ultraviolet radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference in their entirety.

Sunscreens are the most common agents used for sun protection. However, sunscreens also have the disadvantage of preventing or greatly diminishing the cosmetically desirable tanning response. Thus, if an individual uses a sunscreen for protection from ultraviolet radiation, he or she does so at the expense of foregoing a tanned appearance. Furthermore, even if an individual is willing to accept the risks associated with exposure to ultraviolet radiation to obtain a tan, there are situations in which it may not be practical or even possible to do so because of time constraints, weather conditions, etc. Therefore, it would be highly desirable to develop products for providing a tanned appearance to the skin, whenever desired without the need for exposure to ultraviolet radiation.

It is generally known that dihydroxyacetone, when applied topically to human skin, will produce a tanned appearance, i.e. an artificial tan. U.S. Pat. No. 4,708,865, to Turner, issued Nov. 24, 1987 describes the use of hydro- alcoholic solutions of dihydroxyacetone for tanning the skin; U.S. Pat. Nos. 4,466,805, to Welters, issued Aug. 21, 1984 describes hair and skin coloring formulations containing dihydroxyacetone; and 2,949,403, to Andreadis et al., issued Aug. 16, 1960 describes artificial tanning formulations containing dihydroxyacetone in an oleaginous base.

Dihydroxyacetone is relatively sensitive to heat, light, and moisture. It is known that products containing dihydroxyacetone generally have a short shelf life, tending to darken and develop disagreeable off-odors over time, with a concomitant loss of product performance.

Dihydroxyacetone can react with other ingredients in a formulation, especially with nitrogen-containing compounds, such as amines, amino acids, and the like. In fact, without being limited by theory, dihydroxyacetone is believed to provide an artificial tan to human skin by its reaction with the nitrogen containing proteins of the skin. See L. Goldman et al., "Investigative Studies with the Skin Coloring Agents Dihydroxyacetone and Glyoxal", *The Journal of Investigative Dermatology*, vol. 35, pp. 161–164 (1960); E. Wittgenstein et al., "Reaction of Dihydroxyacetone (DHA) with Human Skin Callus and Amino Compounds", *The Journal of Investigative Dermatology*, vol. 36, pp. 283–286 (1961); and A. Meybeck, "A Spectroscopic Study of the Reaction Products of Dihydroxyacetone With Amino Acids", *J. Soc. Cosmet. Chem.*, 25–35 (1977); all of which are incorporated by reference herein in their entirety. These stability and incompatibility problems have limited the scope of artificial tanning products in the past.

Many artificial tanning products also have the disadvantage of not providing the desired control over color development of the tan. Artificial tans are often either too light or too dark, and tend to be too orange, uneven, or unnatural in appearance. Artificial tans often take too long to develop—sometimes as long as several hours or overnight. Also, it is known that some individuals are "non-reactors" or "inadequate reactors" in that these individuals do not develop an artificial tan with dihydoxyacetone or develop an artificial tan to only a slight extent. Therefore, a need exists to develop artificial tanning compositions that are chemically and physically stable, are aestheically pleasing to use, that provide improved color development characteristics, and that provide an artificial tan for non-reacting and inadequately reacting individuals.

It is well known that various chemical compounds can be used to modify or enhance the tanning reaction obtained with dihydroxyacetone on human skin. Examples of such compounds include amino acids. See, e.g. Kawashima et al., "Nonenzymatic Browning Reactions of Dihydroxyacetone With Amino Acids or Their Esters", *Agric. Biol. Chem.* 44(7), 1595–1599 (1980), and M. F. Bobin et al., "Effects of Color Adjuvants On the Tanning Effect of Dihydroxyacetone", *J. Soc. Cosmet. Chem.*, 35 265–272 (August 1984), both of which are incorporated by reference herein in their entirety.

It is generally known that the reaction of dihydroxyacetone with amino acids is difficult to control and has been an obstacle to successfully using amino acids in combination with dihydroxyacetone in an artificial tanning composition. For example, when dihydroxyacetone is formulated with an amino acid, the composition tends to undergo an unacceptable discoloration reaction during storage. A possible solution to this problem is to formulate the dihydroxyacetone separately from the amino acids and to deliver the separate formulations either sequentially from separate containers or simultaneously from a dual-chambered dispensing device.

However, these alternatives are inconvenient, cumbersome, and expensive to implement and use. See, e.g. European Patent No. 527,864, assigned to Unilever, published Jun. 23, 1993.

The present invention utilizes certain amino acids or their pharmaceutically acceptable salts to modify the artificial tanning reaction of dihydroxyacetone with skin to provide improved color development characteristics. The present invention solves the longstanding incompatibility problem between the amino acids (or their pharmaceutically acceptable salts) and dihydroxyacetone through two different types of embodiments. In one set of embodiments, the compositions are formulated at a pH value below about pH 4. Without being limited by theory, it is believed that at these low pH values, the amino acid exists primairly in a form whereby the amino groups are protonated and essentially rendered inactive with the dihydroxyacetone to provide a composition that is suitably stable for storage in a packaged product. Upon application to the skin, it has been found that these stable compositions provide the desired artificial tanning reaction from the dihydroxyacetone, the amino acid, and the skin. It is believed that when these compositions are contacted with the skin, which typically has a pH value greater than about 4, that the protonated amino sites on the amino acid are neutralized and rendered reactive with the dihydroxyacetone to yield the desirable artificial tanning reaction with the skin. See E. T. Bernstein et al., "The Acidity On The Surface Of The Skin", *N.Y. State J. Med.*, vol. 92, pp.436–442 (1942); H. C. Korting et al., "Influence of Repeated Washings With Soap And Synthetic Detergents On pH and Resident Flora Of The Skin Of Forehead And Forearm", *Act. Derm. Venereol (Stockh)*, vol. 67, pp. 41–47 (1987); and A. Zlotogorski, "Distribution Of Skin Surface pH On The Forehead And Cheek Of Adults", *Arch. Dermatol Res.*, vol. 279, pp. 398–401 (1987), all of which are incorporated by reference herein in their entirety, which discuss the skin pH phenomenon.

In other embodiments of the present invention, stable artificial tanning compositions containing dihydroxyacetone and an amino acid are achieved over a wide range of pH values (i.e. not limited to pH values of about 4 or below) by also utilizing a stabilizing salt selected from the group consisting of metabisulfite salts, sulfite salts, and hydrogen sulfite salts. These compositions also provide improved development characteristics.

It is therefore an object of the present invention to provide compositions for imparting an artificial tan to human skin.

It is another object of the present invention to provide artificial tanning compositions formulated below a pH value of about 4 having a high degree of chemical and physical stability comprising both dihydroxyacetone and certain amino acids for modifying the artificial tan development.

It is another object of the present invention to provide artificial tanning compositions having a high degree of chemical and physical stability comprising dihydroxyacetone, certain amino acids, and stabilizing salt selected from the group consisting of metabisulfite salts, sulfite salts, hydrogen sulfite salts, and mixtures thereof.

It is another object of the present invention to provide artificial tanning compositions having improved color development characteristics.

It is another object of the present invention to provide artificial tanning compositions which are aesthetically pleasing to use.

It is another object of the present invention to provide artificial tanning compositions useful for both providing an artificial tan to human skin and for protecting human skin from the harmful effects of ultraviolet radiation.

It is another object of the present invention to provide a method for artificially tanning human skin.

It is another object of the present invention to provide a method for artificially tanning human skin and for providing protection from the harmful effects of ultraviolet radiation.

These and other objects of this invention will become apparent in light of the following disclosure.

SUMMARY OF THE INVENTION

The present invention relates to an artificial tanning composition having improved color development characteristics comprising:
(a) from about 0.1% to about 20% dihydroxyacetone,
(b) from about 0.1% to about 10% of an amino acid or a pharmaceutically acceptable salt thereof selected from the goup consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof, and
(c) a topical carrier, wherein said composition has a pH below about 4.

In other embodiments, the present invention relates to an artificial tanning composition having improved color development characteristics comprising:
(a) from about 0.1% to about 20% dihydroxyacetone,
(b) from about 0.1% to about 10% of an amino acid or a pharmaceutically acceptable salt thereof selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof,
(c) from about 0.025% to about 5% of a stabilizing salt selected from the group consisting of metabisulfite salts, sulfite salts, hydrogen sulfite salts, and mixtures thereof, and
(d) a topical carrier.

All percentages and ratios used herein are by weight of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The compositions of the present invention are useful for providing an artificial tan to human skin. It is found that these compositions have improved color development characteristics and good chemical and physical stability.

By the term "improved color development characteristics" is used herein to mean that the artificial tanning compositions provide a natural-looking tan that rapidly develops on the skin. The term also means that the compositions of the present invention provide an artificial tan for those individuals who tend to show either no tan development or little tan development from conventional artificial tanning products (i.e. for those individuals who can be characterized as "non-reacting" or "inadequately-reacting").

The term "chemical stability", as used herein, means that the various chemical components of the compositions (especially the dihydroxyacetone) do not exhibit appreciable breakdown or degradation. For example, the compositions of the present invention typically retain about 80% or more of the initially added dihydroxyacetone over about a three month period of time at room temperature. The term "physical stability", as used herein, means that the overall composition exhibits physical characteristics such as maintenance of viscosity, resistance to syneresis, resistance to discoloration, resistance to developing off-odors, and in the case of emulsions, resistance to phase separation. For example, the compositions of the present invention typically maintain their physical stability for at least about a three month period of time at room temperature. The terms "chemical stability" and "physical stability" have been separately defined herein for conveninence. Nevertheless, it is realized that these two types of stability phenomena are not necessarily distinct and that chemical stability can impact physical stability and vice versa.

The term "topical application", as used herein, means to apply or spread the artificial composition to the surface of the skin.

The term "pharmaceutically-acceptable", as used herein, means that the compositions or components thereof so described are suitable for use in contact with human tissue without undue toxicity, incompatibility, instability, irritation, allergic response, and the like.

Dihydroxyacetone

The compositions of the present invention comprise from about 0.1% to about 20%, more preferably from about 2% to about 7%, and most preferably from about 3% to about 6% of dihydroxyacetone.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

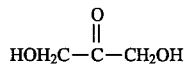

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See *The Merck Index*, Tenth Edition, entry 3167, p. 463 (1983), and "Dihydroxyacetone for Cosmetics", E. Merck Technical Bulletin, 03-304 110, 319 897, 180 588; both of these references being incorporated herein by reference in their entirety.

The scientific literature suggests that the reaction of dihydroxyacetone with the Skin is similar to the Maillard Reaction. In this reaction, reducing sugars react with amino acids, proteins, and peptides to form various adducts which are ultimately converted into brown-colored compounds. See V. R. Usdin, Artificial Tanning Preparations, *Cosmetics and Toiletries*, vol. 91 pp. 29–32 (March 1976), this reference being incorporated herein by reference in Its entirety. Dihydroxyacetone is commercially available from E. Merck (Darmstadt, Germany) and Gist-Brocades Food Ingredients, Inc. (King of Prussia, Pa.). Without being limited by theory, it is believed that dihydroxyacetone reacts with amino acids in the keratin of the skin thereby forming the brown colored compounds which provide an artificial tan. It is believed that the process takes place in the outer layers of the epidermis and that the monomer form of dihydroxyacetone is the active form responsible for this phenomenon. Furthermore, the amino acids formulated into the compositions of the present invention are believed to further modify this tan development.

Amino Acids and Pharmaceutically Acceptable Salts

The compositions of the present invention comprise an amino acid, or a pharmaceutically acceptable salt thereof, selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof. The amino acids or their pharmaceutically acceptable salts comprise from about 0.1% to about 10%, more preferably from about 0.25% to about 5%, and most preferably from about 0.50% to about 1.5% of the compositions herein.

The amino acids and their pharamaceutically acceptable salts described herein are useful for modifying the artificial tan color obtained on human skin using dihydroxyacetone. Dihydroxyacetone is known to react with various nitrogen containing compounds to produce a brown or tan color. See, e.g. Kawashima et al., "Nonenzymatic Browning Reactions of Dihydroxyacetone With Amino Acids or Their Esters", *Agric. Biol. Chem.* 44(7), 1595–1599 (1980), and M. F. Bobin et al., "Effects of Color Adjuvants On the Tanning Effect of Dihydroxyacetone", *J. Soc. Cosmet. Chem.*, 35 265–272 (August 1984), both of which are incorporated by reference herein in their entirety. However, this reaction, has previously been difficult to control and has been an obstacle to formulating a stable artificial tanning composition (i.e. one that does not discolor or develop off-odors) containing both dihydroxyacetone and an amino acid or a salt thereof. A possible solution to this compatibility problem is to formulate the dihydroxyacetone separately from the amino acid and to either deliver the formulations sequentially from separate containers or simultaneously from a dual-chambered dispensing device. However, these alternatives are inconvenient, cumbersome, and expensive. See, e.g. European Patent No. 527,864, assigned to Unilever, published Jun. 23, 1993. In the present invention, stabilized artificial tanning compositions containing amino acids are achieved through compositions formulated at a pH value of less than about 4, or alternatively via compositions which comprise a stabilizing salt selected from the group consisting of metabisulfite salts, sulfite salts, hydrogen sulfite salts, and mixtures thereof (in these alternative embodiments, the pH is not limited to a value of less than about 4).

As described above the amino acids or their pharmaceutically acceptable salts useful herein are those selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof. Preferred are those selected from the group consisting of lysine, arginine, histidine, and mixtures thereof. Most preferred is the amino acid lysine and its pharmaceutically acceptable salts.

Lysine, or a pharmaceutically acceptable salt thereof, is most preferred for use herein, because of the especially natural looking and rapidly developing artificial tan obtained from the addition of this material to a dihydroxyacetone containing composition. Lysine is one of the commonly occurring amino acids and is also known as 2,6-diaminohexanoic acid. Lysine contains two amino groups and a single carboxylic acid group and can be represented by the chemical formula $C_6H_{14}N_2O_2$ and the following chemical structure.

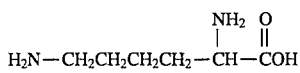

See *The Merck Index*, Tenth Edition, Entry 5453, page 806 (1983), which is incorporated herein by reference in its entirety. Lysine is a compound having a chiral center at the two carbon position and can therefore exist in either the (R) or (S) enatiomeric form. Traditionally, amino acid stereochemistry is also defined in terms of D and L configurations, as is commonly done for carbohydrates. The naturally occurring form of lysine is the L enantiomer, which corresponds to the (S) configuration. The lysine molecule can form salts at its carboxylic acid group with cationic species and at either one or both of its amino groups with anionic species. Because the lysine molecule contains a carboxylic acid group and two amino groups, the molecule therefore exhibits three $pK_a$ values at 2.16, 9.20, and 10.80. It is believed that these $pK_a$ values correspond to the carboxylic acid group, the amino group at the two carbon position, and the amino group at the six carbon position, respectively. The pH of the medium in which the lysine is present will therefore determine whether any of these sites will be in their neutral or ionic form. See A. Streitwieser, Jr. and C. H. Heathcock, *Introduction to Organic Chemistry, Chapter* 28, pp. 814–860, Macmillan Pub..Co., Inc., N.Y., 1976, which is incorporated herein by reference in its entirety.

As described above, most preferred among the amino acids are lysine and its pharmaceutically acceptable salts. Nonlimiting examples of pharmaceutically acceptable lysine salts include lysine sodium salt, lysine potassium salt, lysine calcium salt, lysine magnesium salt, lysine hydrochloride, lysine dihydrochloride, lysine succinate, lysine phosphate, lysine hydrogen sulfate, lysine di(hydrogen sulfate), lysine carbonate, lysine hydrogen carbonate, lysine di(hydrogen carbonate), and mixtures thereof. It is found that among these salts that lysine hydrochloride and lysine dihydrochloride are preferred.

Metabisulfite, Sulfite, and Hydrogen Sulfite Stabilizing Salts

It is found in the present invention that certain stabilizing antioxidant salt materials such as metabisulfite, sulfite, and hydrogen sulfite salts provide an unexpected enhancement of the stability of the compositions. Metabisulfite salts are known as anti-oxidants in the pharmaceutical area, but their use has typically been at extremely low levels, e.g. 0.005%. In the present invention, it is found that much higher levels of metabisulfite and other related salts, i.e. levels in the range from about 0.025% to about 5%, greatly enhance the stability of dihydroxyacetone and lysine containing compositions.

Therefore, in further embodiments, the compositions of the present invention comprise from about 0.025% to about 5%, preferably from about 0.05% to about 5%, more preferably from about 0.05% to about 1%, even more preferably from about 0.1% to about 1%, and most preferably about 0.25% of a salt selected from the group consisting of metabisulfite salts, sulfite salts, hydrogen sulfite salts, and mixtures thereof. In these further embodiments containing a salt selected from the group consisting of metabisulfite, sulfite, and hydrogen sulfite salts, these compositions are not restricted to having a pH value of less than about 4.

A metabisulfite salt contains the metabisulfite anion (also known as the pyrosulfite anion) which corresponds to the chemical formula $(S_2O_5)^{2-}$. A sulfite salt contains the sulfite anion which corresponds to the chemical formula $(SO_3)^{2-}$. A hydrogen sulfite salt contains the hydrogen sulfite anion (also known as the bisulfite anion) which corresponds to the chemical formula $(HSO_3)^-$. These salts also contain a cation and can be represented by the general chemical formula $X^{p+}_m(S_2O_5)^{2-}_n$ for metabisulfite salts, $X^{p+}_m(SO_3)^{2-}_n$ for sulfite salts, and $X^{p+}_m(HSO_3)^-_n$, for hydrogen sulfite salts wherein X corresponds to the cation, and m and n are integer values (i.e. 1, 2, 3, 4, etc.) representing the relative ratio of cations to anions in the salt, and p+ represents the value of the positive charge on the cation (i.e. +1, +2, +3, +4, etc.). It is well known to a chemist of ordinary skill in the art that in the general chemical formulas depicted for these salts, the values for m and n are such that the overall charge on the salt is neutral. For example, sodium metabisulfite can be represented by the chemical formula $Na_2S_2O_5$, wherein two sodium cations (each having a +1 charge) are present for each each metabisulfite anion (having a −2 charge). Sodium sulfite can be represented by the chemical formula $Na_2SO_3$, wherein two sodium cations (each having a +1 charge) are present for each sulfite anion (having a −2 charge). Sodium hydrogen sulfite can be represented by the chemical formula $NaHSO_3$, wherein one sodium cation (having a +1 charge) is present for each hydrogen sulfite anion (having a −1 charge). Calcium metabisulfite can be represented by the chemical formula $Ca(S_2O_5)$ wherein one calcium cation (having a +2 charge) is present for each metabisufite anion (having a −2 charge). Aluminum metabisulfite can be represented by the chemical formula $Al_2(S_2O_5)_3$ wherein two aluminum cations (each having a +3 charge) are present for each three metabisulfite anions (each having a −2 charge). See also *The Merck Index*, Tenth Edition, (1983), Sodium Metabisulfite, Entry 8476, p. 1237, Sodium Sulfite, Entry 8528, p.1242, and Sodium Bisulfite, Entry 8419, p. 1231, all of which are incorporated by reference herein in their entirety.

Metabisulfite, sulfite, and hydrogen sulfite salts useful herein include those selected from the group consisting of alkali metal salts (for example lithium, sodium, potassium, and the like), alkaline metal salts (for example berylium, magnesium, calcium, and the like), ammonium salts, and mixtures thereof. The ammonium salts are defined herein to encompass those salts containing both the unsubstituted ammonium cation (i.e. $NH_4^+$) as well as various substituted ammonium cations. Nonlimiting examples of substituted ammonium cations include alkyl ammonium cations such as monoalkyl, dialkyl, trialkyl, and tetralkyl ammonium cations wherein the alkyl groups are independently selected from straight and branched chain alkyl groups having from about 1 to about 30 carbon atoms. Other examples of substituted ammonium cations include alkanol ammonium cations such as monoalkanol, dialkanol, trialkanol, and tetraalkanol ammonium cations wherein the alkanol groups are independently selected from straight and branched chain alkanol groups having from about 2 to about 30 carbon atoms. Nonlimiting examples of substituted alkyl ammonium and alkanol ammonium cations include methyl ammonium, ethyl ammonium, dimethyl ammonium, diethyl ammonium, trimethyl ammonium, triethyl ammonium, tetramethyl ammonium, tetraethylammonium, dimethyl distearyl ammonium, monoethanol ammonium, diethanol ammonium, triethanol ammonium, tetraethanol ammonium, monoethanoltrimethyl ammonium cations, and mixtures thereof.

Among the metabisulfite, sulfite, and hydrogen sulfite salts useful herein, the metabisulfite salts are preferred. Preferred metabisulfite salts include those selected from the group consisting of sodium metabisulfite (i.e. $Na_2S_2O_5$), potassium metabisulfite (i.e. $K_2S_2O_5$), ammonium metabisulfite [i.e. $(NH_4)_2(S_2O_5)$], and mixtures thereof. Most preferred is sodium metabisulfite.

Topical Carrier

The compositions of the present invention comprise as an essential component a topical carrier carrier or diluent which can be of a variety of different forms. The term "topical carrier" means a vehicle or base composition for containing, delivering, or carrying the essential components and any additional or optional components of the present invention to the surface of the skin. The topical carrier should be one that is pharmaceutically acceptable because of its intended use on human skin. The topical carrier can contain a wide variety of common pharmaceutical and cosmetic ingredients typically used in the beauty care industry, nonlimiting examples of which are described below. The topical carrier can be in the form of an emulsion including, but not limited to, oil-in-water, water-in-oil, water-in-oil-in-water, water-in-silicone and oil-in-water-in-silicone emulsions. These emulsions can cover a broad range of consistencies including thin lotions (which can also be suitable for aerosol or nonaerosol spray delivery), creamy lotions, light creams, heavy creams, and the like. The topical carrier can also comprise an aqueous-based system containing other water-soluble solvents such as alcohols. These aqueous-based systems can be formulated over a wide range of viscosities and can be thickened with a wide variety of water-compatible thickening agents to form viscous liquids and gels. The lower viscosity aqueous-based systems can also be delivered as aerosol and nonaerosol sprays. The viscosity of the compositions herein will therefore vary depending upon the exact ingredients chosen and the type of carrier desired. For example, the viscosity of the compositions herein can range from about 0.1 cps to about 5,000,000 cps, or more. Nonlimiting examples of topical carriers useful in the present invention are described in the following four references all of which are incorporated herein by reference in their entirety: "Sun Products Formulary" *Cosmetics & Toiletries*, vol. 105, pp. 122–139 (December 1990); "Sun Products Formulary", *Cosmetics & Toiletries*, vol. 102, pp. 117–136 (March 1987); U.S. Pat. Nos. 4,960,764 to Figueroa et al., issued Oct. 2, 1990; and 4,254,105 to Fukuda et al., issued Mar. 3, 1981.

The topical carrier can also comprise an oil-in-water emulsion system having complex structures such as liquid crystals and crystalline gel networks. The nature of liquid crystals, the formation of liquid crystals, the properties and the advantages of liquid crystals are described further in G. Dahms, Properties of O/W Emulsions With Anisotropic Lamellar Phases, 101 *Cosmetics & Toiletries*, 113–115 (1986); P. Loll, Liquid Crystals in Cosmetic Emulsions, *ICI Surfactants' Publication RP94-93E*; and G. M. Eccleston, Multiple-Phase Oil-In-Water Emulsions, 41, *J. Soc. Cosmet. Chem.*, 1–22, (January/February 1990); all of which are incorporated herein by reference in their entirety.

The exact level of the topical carrier employed will vary depending upon the carrier chosen, the levels of the essential components, and the levels of any optional components. The topical carrier preferably comprises from about 50% to about 99.8% in those embodiments not comprising the stabilizing salt selected from the group consisting of metabisulfite salts, sulfite salts, and hydrogen sulfite salts, and from about 50% to about 99.775% of those embodiments comprising the stabilizing salt selected from the group consisting of metabisulfite salts, sulfite salts, and hydrogen sulfite salts. In all embodiments, the topical carrier more preferably comprise from about 70% to about 99%, and most preferably from about 75% to about 96%, of the compositions.

pH Of The Compositions

In those embodiments of the present invention not comprising the stabilizing salt selected from the group consisting of metabisulfite salts, sulfite salts, and hydrogen sulfite salts, the compositions of the present invention have a pH less than about 4, preferably from about 2.5 to about 3.99, and more preferably from about 3.0 to about 3.5. An acidic buffer system can be used, but is not required, in helping to maintain the desired pH of the compositions. Nonlimiting examples of acidic buffer systems useful herein include those selected from the group consisting of citrate, acetate, phosphate, and benzoate buffers.

In those embodiments wherein the compositions comprise a stabilizing salt selected from the group consisting of metabisulfite salts, sulfite salts, and hydrogen sulfite salts, the pH of the present invention can encompass a wide range of pH values (including pH values of about 4 or greater), although the compositions preferably have a pH from about 2.5 to about 7, more preferably from about 2.5 to about 6, and most preferably from about 3.5 to about 5.

It is well known to one of ordinary skill in the art that the pH of an aqueous system is readily measured utilizing pH meters and commercially available indicator papers. In the case of aqueous systems, the pH value is readily made on the aqueous phase. In the case of primarily non-aqueous systems, e.g. in emulsion systems having a continuous oil phase (i.e. water-in-oil emulsions) the pH value would correspond to the internal water phase of such systems.

Additional Components

The compositions of the present invention can comprise a wide range of additional components. These additional components can comprise the topical carrier itself or can comprise components which are delivered from the topical carrier.

The *CTFA Cosmetic Ingredient Handbook*, Second Edition, 1992, which is incorporated by reference herein in its entirety, describes a wide variety of nonlimiting cosmetic and pharmceutical ingredients commonly used in the beauty care industry, which are suitable for use in the compositions of the present invention. Nonlimiting examples of functional classes of ingredients are described at page 537 of this reference. Examples of these functional classes include: abrasives, absorbents, antiacne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, emulsion stabilizers, external analgesics, film formers, fragrance components, humectants, opacifying agents, pH adjusters, preservatives, propellants, reducing agents, skin bleaching agents, skin-conditioning agents (emollients, humectants, miscellaneous, and occulsive), skin protectants, solvents, sunscreen agents, surfactants (cleansing agents, emulsifying agents, foam boosters, hydrotropes, solubilizing agents, suspending agents, and nonsurfactants), ultraviolet light absorbers, viscosity decreasing agents, and viscosity increasing agents (aqueous and nonaqueous).

Some nonlimiting examples of these additional components cited in the *CTFA Cosmetic Ingredient Handbook*, as well as other materials useful herein, include the following: vitamins and derivatives thereof (e.g tocopherol, tocopherol acetate, retinoic acid, retinol, retinoids, and the like); thickening agents; crosslinked acrylic acid homopolymers available as the carbomers from B. F. Goodrich; acrylates/C10–30 alkyl acrylate crosspolymers available as Carbopol 1342 from B. F. Goodrich; gums; waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220$^R$); preservatives for maintaining the antimicrobial integrity of the compositions; skin penetration aids such as DMSO, 1-dodecylazacycloheptan-2-one (available as Azone from the Upjohn Co.) and the like; anti-acne medicaments (e.g., resorcinol, salicylic acid, erythromycin, benzoyl peroxide, zinc, and the like); skin bleaching (or lightening) agents including but not limited to hydroquinone, kojic acid; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabolol, dipotassium glycyrrhizinate and the like; and skin conditioning agents such as the propoxylated glycerols described in U.S. Pat. No. 4,976,953, to Orr et al., issued Dec. 11, 1990, which is incorporated by reference herein in its entirety. Especially preferred optional ingredients include sunscreen agents as further described below.

Sunscreen Agents

The compositions of the present invention can also comprise one or more sunscreen agents. When a sunscreen agent is employed, it is found that the compositions of the present invention are also useful for protecting human skin from the harmful effects of ultraviolet radiation.

The sunscreen agent can comprise from about 0.1% to about 30%, more preferably from about 0.5% to about 25%, and most preferably from about 1% to about 20% of the composition. Exact amounts of sunscreen agent will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register*, Vol. 43, No. 166, pp. 38206–38269, Aug. 25, 1978, which is incorporated herein by reference in its entirety.

A wide variety of sunscreen agents are useful herein. These sunscreen agents include both organic compounds and their salts as well as inorganic particulate materials. Without being limited by theory, it is believed that sunscreen agents provide protection from ultraviolet radiation by one or more of the following mechanisms including absorption, scattering, and reflection of the ultraviolet radiation. Nonlimiting examples of these sunscreen agents are described in U.S. Pat. Nos. 5,087,445, to Haffey et al., issued Feb. 11, 1992; 5,073,372, to Turner et al., issued Dec. 17, 1991; 5,073,371, to Turner et al. issued Dec. 17, 1991; 5,160,731, to Sabatelli et al., issued Nov. 3, 1992; 5,138,089, to Sabatelli, issued Aug. 11, 1992; 5,041,282, to Sabatelli, issued Aug. 20, 1991; 4,999,186, to Sabatelli et al., issued Mar. 12, 1991; 4,937,370, to Sabatelli, issued Jun. 26, 1990; and Segarin, et al., at Chapter VIII, pages 189 et seq., of *Cosmetics Science and Technology*; all of these documents being incorporated herein by reference in their entirety. Preferred among the sunscreen agents are those selected from the group consisting of 2-ethylhexyl p-methoxycinnamate, octyl salicylate, octocrylene, oxybenzone, 2-ethylhexyl N,N-dimethylaminobenzoate, p-aminobenzoic acid, 2-phenyl-benzimidazoleo5-sulfonic acid, homomenthyl salicylate, DEA p-methoxycinnamate, 4,4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy)benzophenone, 4-N,N-dimethylaminobenzoic acid ester with 4-hydroxydibenzoyl- methane, 4-N,N-dimethylaminobenzoic acid ester with 4-(2-hydroxyethoxy)dibenzoylmethane, 4-N,N-di(2-ethylhexyl)aminobenzoic acid ester with 2,4-dihydroxybenzophenone, 4-N,N-di(2-ethylhexyl)aminobenzoic acid ester with 2-hydroxy-4-(2-hydroxyethoxy)benzophenone, 4-N,N-di(2-ethylhexyl)aminobenzoic acid ester with 4-hydroxydibenzoylmethane, 4-N,N-di(2-ethylhexyl)aminobenzoic acid ester with 4-(2-hydroxyethoxy)dibenzoylmethane, 4-N,N-(2-ethylhexyl)methylaminobenzoic acid ester with 2,4-dihydroxybenzophenone, 4-N,N-(2-ethylhexyl)methylaminobenzoic acid ester with 2-hydroxy-4-(2-hydroxyethoxy)benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane, titanium dioxide, zinc oxide, iron oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, zinc oxide, iron oxide, and mixtures thereof.

Most preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-buyldibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, zinc oxide, iron oxide, and mixtures thereof.

Methods for Providing an Artificial Tan and for Protecting the Skin from UV Radiation The compositions of the present invention are useful for providing an artificial tan to human skin. These compositions, when optionally formulated to contain sunscreen compounds as described above, are also useful for protecting human skin from the harmful effects of ultraviolet radiation. To obtain an artificial tan and/or protection from the harmful effects of UV radiation, an effective amount of the composition of the present invention is applied to the skin. The term "effective" means an amount of the present compositions to provide an artificial tan and/or protection from ultraviolet radiation, but not so much as to cause any undesirable side effects or skin reactions. The term "protection" means that the present compositions attenuate or reduce the amount of ultraviolet radiation reaching the skin's surface thereby reducing the incidence of undesirable skin reactions such as sunburn, erythema, skin cancer, and photoinduced skin aging. As described above, one commonly used measure of a compositions effectiveness against ultraviolet radiation is the SPF factor.

A wide range of quantities of the compositions of the present invention can be employed to provide an artificial tan and/or protection from the harmful effects of ultraviolet radiation. Quantities of the present composition which are typically applied to provide an artificial tan and/or protection from the harmful effects of ultraviolet radiation can range from about 0.1 mg/cm² to about 10 mg/cm². A particularly useful amount to use is about 2 mg/cm².

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES I–III

Artificial Tanning Creams Containing Dihydroxyacetone and Lysine and Formulated To a pH Value of Below About 4

An oil-in-water emulsion is prepared by combining the following ingredients using conventional mixing techniques. Examples I, II and III correspond to light, medium, and dark artificial tanning creams, respectively.

| Examples Ingredients | I | II | III |
|---|---|---|---|
| | | Weight Percent | |
| PHASE A | | | |
| Water | qs 100 | qs 100 | qs 100 |
| Glycerin | 5.00 | 5.00 | 5.00 |
| Magenisum Aluminum Silicate | 0.50 | 0.50 | 0.50 |
| Xanthan Gum | 0.30 | 0.30 | 0.30 |
| Disodium EDTA | 0.10 | 0.10 | 0.10 |
| Acrylates/C10–30 Alkyl Acrylate Crosspolymer | 0.025 | 0.025 | 0.025 |
| PHASE B | | | |
| Octyl Palmitate | 3.00 | 3.00 | 3.00 |
| PPG-20 Methyl Glucose Ether Distearate | 2.00 | 2.00 | 2.00 |
| Cetyl Alcohol | 2.00 | 2.00 | 2.00 |
| Stearyl Alcohol | 2.00 | 2.00 | 2.00 |
| Polysorbate 60 | 1.00 | 1.00 | 1.00 |
| Dimethicone | 1.00 | 1.00 | 1.00 |
| Steareth-20 | 1.00 | 1.00 | 1.00 |
| Glyceryl Stearate (and) | 0.25 | 0.25 | 0.25 |
| DEA-Cetyl Phosphate | 0.10 | 0.10 | 0.10 |
| PHASE C | | | |
| Water | 10.5 | 11.5 | 13.5 |
| Dihydroxyacetone | 3.00 | 4.00 | 5.00 |
| Butylene Glycol | 2.50 | 2.50 | 2.50 |
| Citric Acid | 2.00 | 2.00 | 2.00 |
| L-Lysine | 0.50 | 0.50 | 0.50 |
| DMDM Hydantoin (and) Iodopropylnyl Butylcarbamate | 0.25 | 0.25 | 0.25 |
| PHASE D | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is stirred for 15 minutes while maintaining a temperature of 70°–75° C. The emulsion is then allowed to cool to 40° C. In a separate vessel the ingredients of Phase C are added and stirred until all are dissolved. Phase C is next added and stirring is continued for 15 minutes. When the emulsion is at 35° C., Phase D is added and stirring is continued until cooled to room temperature.

The resulting creams have a pH less than about 4, exhibit good physical and chemical stability, improved color development characteristics, and are useful for topical application to human skin to provide an artificial tan.

In variations on these formulas the L-lysine is varied over the range from about 0.5% to about 1.5% by weight of the total composition. In other variations on these formulas, the L-lysine is replaced with an equivalent weight of L-lysine hydrochloride or L-lysine dihydrochloride or other amino acids or their pharmaceutically acceptable salts such as arginine and histidine. Also, in other variations, from about 0.025% to about 5% of one of the following salts is added: sodium metabisulfite, sodium sulfite, sodium bisulfite, potassium metabisulfite, or ammonium metabisulfite.

EXAMPLES IV–VI

Artificial Tanning Creams Containing Sunscreens and Formulated To A pH Value Below About 4

An oil-in-water emulsion is prepared by combining the following ingredients using conventional mixing techniques. Examples IV, V, and VI correspond to light, medium, and dark artificial tanning creams, respectively.

| Examples Ingredients | IV | V | VI |
|---|---|---|---|
| | | Weight Percent | |
| PHASE A | | | |
| Water | qs 100 | qs 100 | qs 100 |
| Glycerin | 5.00 | 5.00 | 5.00 |

-continued

| Examples Ingredients | IV | V | VI |
|---|---|---|---|
| | Weight Percent | | |
| Magenisum Aluminum Silicate | 0.50 | 0.50 | 0.50 |
| Xanthan Gum | 0.30 | 0.30 | 0.30 |
| Disodium EDTA | 0.10 | 0.10 | 0.10 |
| Acrylates/C10–30 Alkyl Acrylate Crosspolymer | 0.025 | 0.025 | 0.025 |
| PHASE B | | | |
| Octyl Palmitate | 3.00 | 3.00 | 3.00 |
| 2-Ethylhexyl-p-methoxycinnamate | 2.00 | 2.00 | 2.00 |
| Oxybenzone | 1.00 | 0.00 | 0.00 |
| Octocrylene | 1.00 | 0.00 | 0.00 |
| PPG-20 Methyl Glucose Ether Distearate | 2.00 | 2.00 | 2.00 |
| Cetyl Alcohol | 2.00 | 2.00 | 2.00 |
| Stearyl Alcohol | 2.00 | 2.00 | 2.00 |
| Polysorbate 60 | 1.00 | 1.00 | 1.00 |
| Dimethicone | 1.00 | 1.00 | 1.00 |
| Steareth-20 | 1.00 | 1.00 | 1.00 |
| Glyceryl Stearate (and) | 0.25 | 0.25 | 0.25 |
| DEA-Cetyl Phosphate | 0.10 | 0.10 | 0.10 |
| PHASE C | | | |
| Water | 10.5 | 11.5 | 13.5 |
| Dihydroxyacetone | 3.00 | 4.00 | 5.00 |
| Butylene Glycol | 2.50 | 2.50 | 2.50 |
| Citric Acid | 2.00 | 2.00 | 2.00 |
| L-Lysine | 0.50 | 0.50 | 0.50 |
| DMDM Hydantoin (and) Iodopropylnyl Butyl-carbamate | 0.25 | 0.25 | 0.25 |
| PHASE D | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is stirred for 15 minutes while maintaining a temperature of 70°–75° C. The emulsion is then allowed to cool to 40° C. In a separate vessel the ingredients of Phase C are added and stirred until all are dissolved. Phase C is next added and stirring is continued for 15 minutes. When the emulsion is at 35° C., Phase D is added and stirring is continued until cooled to room temperature.

The resulting creams have a pH less than about 4, exhibit good physical and chemical stability and improved color development characteristics, and are useful for topical application to human skin to provide an artificial tan and protection against ultraviolet radiation.

In variations on these formulas the L-lysine is varied over the range from about 0.5% to about 1.5% by weight of the total composition. In other variations on these formulas, the L-lysine is replaced with an equivalent weight of L-lysine hydrochloride or L-lysine dihydrochloride or other amino acids or their pharmaceutically acceptable salts such as arginine and histidine. Also, in other variations, from about 0.025% to about 5% of one of the following salts is added: sodium metabisulfite, sodium sulfite, sodium bisulfite, potassium metabisulfite, or ammonium metabisulfite.

EXAMPLES VII–IX

Artificial Tanning Gel Network Emulsions Containing Dihydroxyacetone and Lysine Hydrochloride An oil-in-water emulsion is prepared by combining the following ingredients using conventional mixing techniques. Examples VII, VIII, and IX correspond to light, medium, and dark artificial tanning creams, respectively.

| Examples Ingredients | VII | VIII | IX |
|---|---|---|---|
| | Weight Percent | | |
| PHASE A | | | |
| Water | qs 100 | qs 100 | qs 100 |
| Glycerin | 5.00 | 5.00 | 5.00 |
| Cetyl Hydroxyethylcellulose | 0.15 | 0.15 | 0.15 |
| Disodium EDTA | 0.10 | 0.10 | 0.10 |
| Xanthan Gum | 0.10 | 0.10 | 0.10 |
| PHASE B | | | |
| Cetyl Alcohol | 2.13 | 2.13 | 2.13 |
| Behenyl Alcohol | 2.13 | 2.13 | 2.13 |
| Isohexadecane | 1.00 | 1.00 | 1.00 |
| PPG-3 Myristyl Ether | 1.00 | 1.00 | 1.00 |
| Cyclomethicone D5 | 1.00 | 1.00 | 1.00 |
| Ceteareth-20 | 0.45 | 0.45 | 0.45 |
| Ceteareth-12 | 0.30 | 0.30 | 0.30 |
| PHASE C | | | |
| Water | 9.00 | 10.00 | 12.00 |
| Dihydroxyacetone | 3.30 | 4.30 | 5.30 |
| Butylene Glycol | 2.50 | 2.50 | 2.50 |
| L-Lysine Hydrochloride | 0.75 | 0.75 | 0.75 |
| DMDM Hydantoin (and) Iodopropylnyl Butyl-carbamate | 0.25 | 0.25 | 0.25 |
| Sodium Metabisulfite | 0.25 | 0.35 | 0.45 |
| PHASE D | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is homogenized for 15 minutes while maintaining a temperature of 70°–75° C. The emulsion is then allowed to cool to 40° C. In a separate vessel the ingredients of Phase C are added and stirred until all are dissolved. Phase C is next added and stirring is continued for 15 minutes. When the emulsion is at 35° C., Phase D is added, and the emulsion is cooled to room temperature with stirring.

The resulting compositions exhibit good physical and chemical stability, improved color development characteristics, and are useful for topical application to human skin to provide an artificial tan.

In variations on these formulas the L-lysine hydrochloride is varied over the range from about 0.5% to about 1.5% by weight of the total composition. In other variations on these formulas, the L-lysine hydrochloride is replaced with an equivalent weight of L-lysine or L-lysine dihydrochloride or other amino acids or their pharmaceutically acceptable salts such as arginine and histidine. Also, in other variations, from about 0.025% to about 5% of one of the following salts is added: sodium metabisulfite, sodium sulfite, sodium bisulfite, potassium metabisulfite, or ammonium metabisulfite.

What is claimed is:

1. An artificial tanning composition having improved color development comprising a mixture of:
   (a) from about 0.1% to about 20% dihydroxyacetone,
   (b) from about 0.1% to about 10% of an amino acid or pharmaceutically acceptable salt thereof selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof, and (c) a topical carrier, wherein said composition has a pH below about 4.

2. A composition according to claim 1 wherein said amino acid or pharmaceutically acceptable salt thereof is selected from the group consisting of lysine, arginine, histidine, and mixtures thereof.

3. A composition according to claim 1 wherein said amino acid or pharmaceutically acceptable salt thereof is selected from the group consisting of L-lysine, L-lysine hydrochloride, L-lysine dihydrochloride, or mixtures thereof.

4. A composition according to claim 3 comprising from about 0.25% to about 5% of said amino acid or pharmaceutically acceptable salt thereof.

5. A composition according to claim 3 comprising from about 0.50% to about 1.5% of said amino acid or pharmaceutically acceptable salt thereof.

6. A composition according to claim 5 wherein the pH of said composition is from about 2.5 to about 3.99.

7. A composition according to claim 5 wherein the pH of said composition is from about 3 to about 3.5

8. A composition according to claim 7 comprising from about 2% to about 7% dihydroxyacetone.

9. A composition according to claim 7 comprising from about 3% to about 6% dihydroxyacetone.

10. A composition according to claim 1 wherein said composition further comprises from about 0.5% to about 20% of a sunscreen selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-buyl-dibenzoylmethane, 3-(4-methylbenzylidene) camphor, 3-benzylidene camphor, 4-N,N-(2-ethylhexyl)methylaminobenzoic acid ester with 4-(2-hydroxyethoxy-)dibenzoylmethane, titanium dioxide, zinc oxide, iron oxide, and mixtures thereof.

11. A method for providing an artificial tan to human skin comprising topically applying to the skin an effective amount of a composition according to claim 1.

12. A method for providing an artificial tan to human skin and protecting human skin from the harmful effects of ultraviolet radiation comprising topically applying to the skin an effective amount of a composition according to claim 10.

13. An artificial tanning composition having improved color development comprising a mixture of:

(a) from about 0.1% to about 20% dihydroxyacetone, (b) from about 0.25% to about 5% of an amino acid or pharmaceutically acceptable salt thereof selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof, (c) from about 0.1% to about 5% of a stabilizing salt selected from the group consisting of metabisulfite salts, sulfite salts, hydrogen sulfite salts, and mixtures thereof, and (d) a topical carrier.

14. A composition according to claim 13 wherein said amino acid or pharmaceutically acceptable salt thereof is selected from the group consisting of lysine, arginine, histidine, and mixtures thereof.

15. A composition according to claim 13 wherein said amino acid or pharmaceutically acceptable salt thereof is selected from the group consisting of L-lysine, L-lysine hydrochloride, L-lysine dihydrochloride, or mixtures thereof.

16. A composition according to claim 15 comprising from about 0.50% to about 1.5% of said amino acid or pharmaceutically acceptable salt thereof.

17. A composition according to claim 16 comprising from about 2% to about 7% dihydroxyacetone.

18. A composition according to claim 16 comprising from about 3% to about 6% dihydroxyacetone.

19. A composition according to claim 18 wherein said metabisulfite, sulfite, and hydrogen sulfite salts are selected from the group consisting of alkali metal salts, alkaline metal salts, ammonium salts, and mixtures thereof.

20. A composition according to claim 18 wherein said metabisulfite, sulfite, and hydrogen sulfite salts are selected from the group consisting of sodium salts, potassium salts, ammonium salts, and mixtures thereof.

21. A composition according to claim 18 wherein said salt selected from the group consisting of metabisulfite salts, sulfite salts, and hydrogen sulfite salts is a metabisulfite salt.

22. A composition according to claim 21 wherein said metabisulfite salt is selected from the group consisting of alkali metal metabisulfite salts, alkaline metal metabisufite salts, ammonium metabisulfite salts, and mixtures thereof.

23. A composition according to claim 21 wherein said metabisulfite salt is selected from the group consisting of sodium metabisulfite, potassium metabisulfite, ammonium metabisulfite, and mixtures thereof.

24. A composition according to claim 23 wherein said metabisulfite salt is sodium metabisulfite.

25. A composition according to claim 21 comprising from about 0.1% to about 1% of said metabisulfite salt.

26. A composition according to claim 21 comprising about 0.25% of said metabisulfite salt.

27. A composition according to claim 13 wherein said composition further comprises from about 0.5% to about 20% of a sunscreen selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-buyl-dibenzoylmethane, 3-(4-methylbenzylidene) camphor, 3-benzylidene camphor, 4-N,N-(2-ethylhexyl)methylaminobenzoic acid ester with 4-(2-hydroxyethoxy-)dibenzoylmethane, titanium dioxide, zinc oxide, iron oxide, and mixtures thereof.

28. A method for providing an artificial tan to human skin comprising topically applying to the skin an effective amount of a composition according to claim 13.

29. A method for providing an artificial tan to human skin and protecting human skin from the harmful effects of ultraviolet radiation comprising topically applying to the skin an effective amount of a composition according to claim 27.

* * * * *

UNITED STATES PATENT AND TRADEMARK OFFICE
CERTIFICATE OF CORRECTION

PATENT NO.        :    5,603,923

DATED             :    February 18, 1997

INVENTOR(S)       :    Larry Richard Robinson, Paul Robert Tanner

It is certified that error appears in the above-identified patent and that said Letters Patent is hereby corrected as shown below:

At column 5, line 54 "Skin" should read --skin--.

At column 5, line 60 "Its" should read --its--.

At column 9, line 59 "Lameliar" should read --Lamellar--.

At column 12, line 20 "benzimidazoleo5-sulfonic" should read --benzimidazole-5-sulfonic--.

At column 13, line 16 "riot" should read --not--.

At column 14, line 11 after "(and)" please insert --PEG-100 Stearate--.

At column 14, line 18 "Iodopropylnyl" should read --Iodopropynyl--.

At column 15, line 19 after "(and)" please insert --PEG-100 Stearate--.

At column 15, line 27 "Iodopropylnyl" should read --Iodopropynyl--.

At column 16, line 25 "Iodopropylnyl" should read --Iodopropynyl--.

At column 18, line 29 "metabisufite" should read --metabisulfite--.

Signed and Sealed this

Twenty-fourth Day of June, 1997

Attest:

BRUCE LEHMAN

*Attesting Officer*     *Commissioner of Patents and Trademarks*